(12) United States Patent
Zhao et al.

(10) Patent No.: US 7,964,359 B2
(45) Date of Patent: Jun. 21, 2011

(54) COMPOSITIONS AND METHODS FOR THE ENHANCEMENT OF SOLUBLE AMYLOID BETA OLIGOMER (ADDL) UPTAKE AND CLEARANCE

(75) Inventors: Wei-Qin Zhao, North Wales, PA (US); Grant A. Krafft, Glenview, IL (US); William L. Klein, Winnetka, IL (US)

(73) Assignees: Acumen Pharmaceuticals, Inc., South San Francisco, CA (US); Northwestern University, Evanston, IL (US)

( * ) Notice: Subject to any disclaimer, the term of this patent is extended or adjusted under 35 U.S.C. 154(b) by 474 days.

(21) Appl. No.: 11/747,324

(22) Filed: May 11, 2007

(65) Prior Publication Data
US 2007/0264669 A1    Nov. 15, 2007

Related U.S. Application Data

(60) Provisional application No. 60/747,163, filed on May 12, 2006.

(51) Int. Cl.
*G01N 33/53* (2006.01)
*A61K 38/28* (2006.01)

(52) U.S. Cl. .......................................... 435/7.1; 514/5.9
(58) Field of Classification Search .......................... None
See application file for complete search history.

(56) References Cited

U.S. PATENT DOCUMENTS

| | | | | |
|---|---|---|---|---|
| 6,313,093 B1 * | 11/2001 | Frey, II | ............................ | 514/12 |
| 2008/0248099 A1 * | 10/2008 | Ishii | ............................ | 424/450 |

OTHER PUBLICATIONS

Alberts et al. 1994. Molecular Biology of the Cell, pp. 129-130.*
Zhao et al. Insulin-degrading enzyme as a downstream target of insulin receptor signaling cascade: implications for Alzheimer's disease intervention. J Neurosci. Dec. 8, 2004;24(49):11120-6.*
Hennige et al. Insulin glulisine: insulin receptor signaling characteristics in vivo. Diabetes. Feb. 2005;54(2):361-6.*
Rickle, Annika, "PTEN and AKT Signalling in Alzheimer's Disease", Karolinska Institutet 2005—Thesis.
Arvanitakis et al., "Diabetes Mellitus and Risk of Alzheimer Disease and Decline in Cognitive Function", Arch Neurol 2004 61:661-666.
Ho et al., "Diet-induced insulin resistance promotes amyloidosis in a transgenic mouse model of Alzheimer's disease", FASEB 2004 18(17):902-904.
Lacor et al., "Synaptic targeting by Alzheimer's-Related Amyloid Beta Oligomers", The Journal of Neuroscience 2004 24(45):10191-10200.

* cited by examiner

*Primary Examiner* — Daniel E Kolker
*Assistant Examiner* — Gregory S Emch
(74) *Attorney, Agent, or Firm* — Licata & Tyrrell P.C.

(57) ABSTRACT

The present invention relates to methods for enhancing the cellular uptake and clearance of soluble oligomeric Aβ peptide assemblies from the environment surrounding both neuronal and non-neuronal cells. Oligomeric Aβ peptide assembly uptake and clearance is achieved via an agent that enhances insulin receptor signaling. Such ADDL uptake enhancers represent effective anti-ADDL therapeutics for use in the therapeutic treatment and/or prophylactic treatment of diseases including Alzheimer's disease, Down's syndrome, and the like, in which compromised nerve cell function is linked to the formation and/or the activity of soluble oligomeric Aβ peptide assemblies, also known as ADDLs, and ADDL-related assemblies.

2 Claims, 7 Drawing Sheets

COMPOSITIONS AND METHODS FOR THE ENHANCEMENT OF SOLUBLE AMYLOID BETA OLIGOMER (ADDL) UPTAKE AND CLEARANCE

This application claims benefit of priority to U.S. Provisional Patent Application Ser. No. 60/747,163, filed May 12, 2006, the content of which is incorporated herein by reference in its entirety.

This invention was made with government support under R01 AG22547 awarded by the National Institutes of Health. The government has certain rights in the invention.

BACKGROUND OF THE INVENTION

Alzheimer's disease (AD) is a progressive and degenerative dementia (Terry, et al. (1991) *Ann. Neurol.* 30(4):572-80; Coyle (1987) in *Encyclopedia of Neuroscience*, Ed. G. Adelman, pp 29-31, Birkhäuser: Boston-Basel-Stuttgart), which in its early stages manifests primarily as a profound inability to form new memories (Selkoe (2002) *Science* 298(5594): 789-91). Prominent neuritic plaques and neurofibrillary tangles have been suggested as the major pathology in brain tissue samples taken at autopsy from a demented patient. However, in spite of the prevalence of plaques, clinical and pathology studies suggest that plaques and fibrils were not responsible for cognitive deficits in AD. For example, careful analysis of plaque number and location revealed little or no correlation with nerve cell loss and cognitive impairment (Terry, et al. (1991) *Ann. Neurol.* 30(4):572-80; Terry, et al. (1999) "Alzheimer Disease", 2$^{nd}$ Edition, Lippincott Williams & Wilkins: Philadelphia, Pa.; McLean, et al. (1999) *Ann. Neurol.* 46(6):860-6; Hibbard & McKeel, Jr. (1997) *Anal. Quant. Cytol. Histol.* 19(2):123-38; Sze, et al. (1997) *J. Neuropathol. Exp. Neurol.* 56(8):933-44), and analysis of total amyloid load showed little correlation with disease severity (Giannakopoulos, et al. (2003) *Neurology* 60(9):1495-500). As transgenic mouse models capable of substantial amyloid β (Aβ) 1-42 overproduction emerged, it became clear that significant behavioral deficits developed in these mice long before Aβ deposits or plaque pathology appeared. The parameter that correlated best with behavioral deficits was synaptic deterioration, a process with no apparent link to plaques or Aβ deposition (Mucke, et al. (2000) *J. Neurosci.* 20(11):4050-8; Hsia, et al. (1999) *Proc. Natl. Acad. Sci. USA* 96(6):3228-33; Kawarabayashi, et al. (2001) *J. Neurosci.* 21(2):372-81; Ashe (2005) *Biochem. Soc. Trans.* 33(Pt. 4):591-4).

Plaque-independent functional deficits have been suggested (Oda, et al. (1995) *Exp Neurol.* 136(1):22-31), wherein soluble Aβ complexes are the relevant molecular pathogens in AD, rather than Aβ fibrils. Such complexes are generated by mixing small amounts of clusterin (apoJ) with aqueous solutions of Aβ 1-42, resulting in substantially reduced fibril formation. The disconnection between amyloid fibrils and neurotoxicity was established with the isolation, characterization, and analysis of neurotoxic soluble oligomeric assemblies of Aβ 1-42 (U.S. Pat. No. 6,218,506; Lambert, et al. (1998) *Proc. Natl. Acad. Sci. USA* 95(11):6448-53), also referred to as amyloid-β derived diffusible ligands (ADDLs).

Soluble oligomeric assemblies of Aβ 1-42 assemble from relatively low concentrations of Aβ 1-42, and block LTP in intact animals or in hippocampal slice cultures (Lambert, et al. (1998) *Proc. Natl. Acad. Sci. USA* 95(11):6448-53; Wang, et al. (2002) *Brain Res.* 924(2):133-40; Wang, et al. (2004) *J. Neurosci.* 24(13):3370-8). These oligomeric assemblies exert their memory-compromising activity, at least in part, by binding specifically to dendritic spines on hippocampal neurons (Lacor, et al. (2004) *J. Neurosci.* 24(45):10191-200) and they elevate phosphorylation of tau at AD-specific epitopes (Shughrue, et al. (2005) 2005 *Abstract Viewer/Itinerary Planner Program No.* 209.16 Washington, D.C.: Society for Neuroscience). Soluble oligomeric assemblies of Aβ 1-42 are substantially elevated in AD brain (Gong, et al. (2003) *Proc. Natl. Acad. Sci. USA* 100(18):10417-22) and in cerebrospinal fluid from AD-diagnosed individuals (Georganopoulou, et al. (2005) *Proc. Natl. Acad. Sci. USA* 102(7):2273-6), providing evidence that ADDLs are the relevant molecular pathogens in AD.

As the likely molecular cause of AD, soluble oligomeric assemblies of Aβ 1-42 represent the optimal target for therapy or prophylaxis of AD, mild cognitive impairment, Down's syndrome and other related diseases such as stroke-associated memory loss and the like. Therefore, there is a need in the art for agents which modulate the assembly or activity of soluble oligomeric assemblies of Aβ 1-42.

SUMMARY OF THE INVENTION

The present invention is a method for enhancing the cellular uptake of soluble amyloid beta oligomers. The method involves contacting a cell which expresses an insulin receptor with an agent that enhances insulin receptor signaling thereby enhancing cellular uptake of soluble amyloid beta oligomers. In one embodiment, the agent is insulin.

The present invention also relates to a method for treating a disease associated with soluble amyloid beta oligomers. This method involves administering to a subject in need of treatment an effective amount of an agent that enhances cellular uptake of soluble amyloid beta oligomers in the brain of the subject thereby treating the disease associated with soluble amyloid beta oligomers. In particular embodiments, the agent is insulin.

A method for identifying an agent which modulates cellular uptake of soluble amyloid beta oligomers is also embraced by the present invention. This method involves contacting a cell which expresses an insulin receptor with a test agent in the presence of soluble amyloid beta oligomers and determining whether the test agent increases or decreases removal of the soluble amyloid beta oligomers from the environment surrounding the cell thereby identifying an agent which modulates cellular uptake of soluble amyloid beta oligomers.

Figure 3:
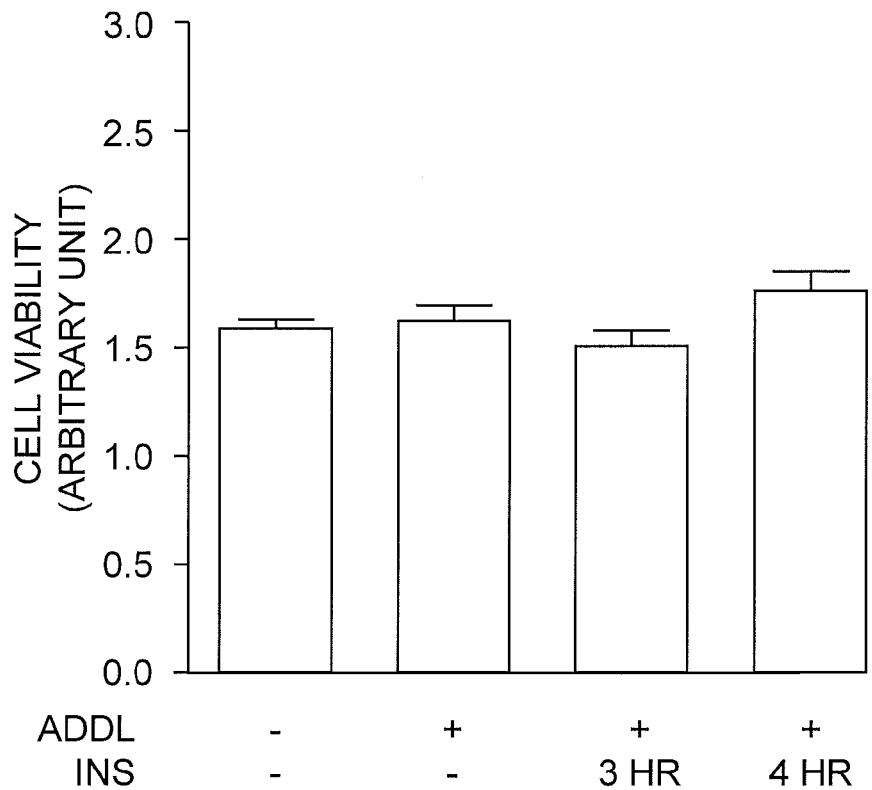

FIG. 3 shows that soluble oligomeric Aβ peptide assemblies cause neuronal toxicity in a treatment duration-dependent (MTT cell viability assay). Insulin-induced oligomeric Aβ peptide assembly uptake did not show an apparent toxic effect.

Figure 4:
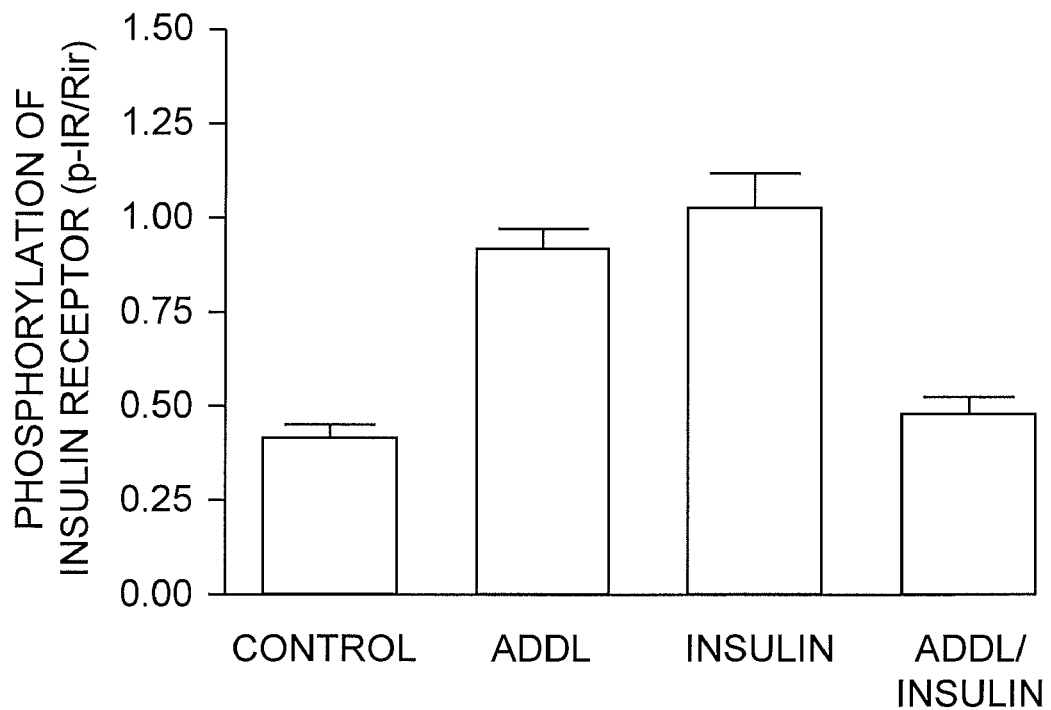

FIG. 4 shows phosphorylation of insulin receptors in neuronal cells after treatment with synthetic soluble oligomeric Aβ peptide assemblies (ADDLs, 50 nM), insulin (100 nM), and oligomeric Aβ peptide assemblies followed by insulin. The insulin receptor was immunoprecipitated by an antibody against the β subunit of the insulin receptor. The precipitated proteins were then detected on separate western blots by an anti-phosphotyrosine antibody and an anti-insulin receptor β subunit antibody, respectively. The ratio of phosphorylated and regular receptors was calculated after densitometry scan and compared among different treatments.

Figure 5A:
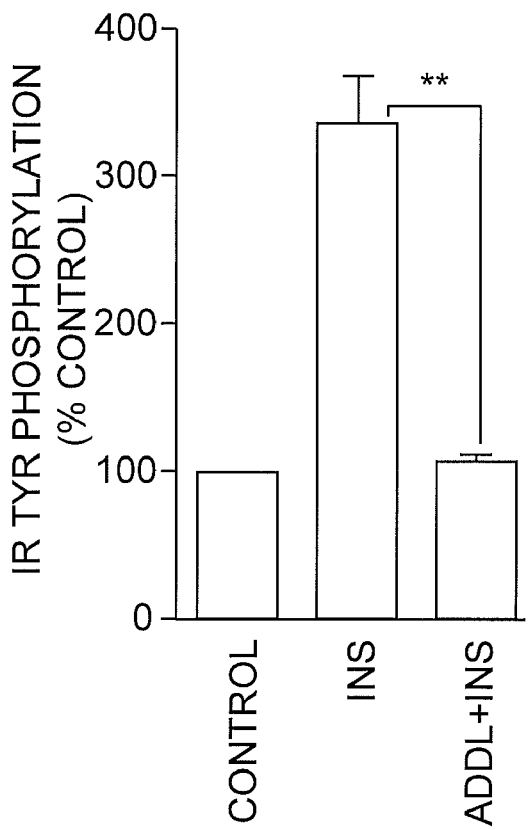
Figure 5B:
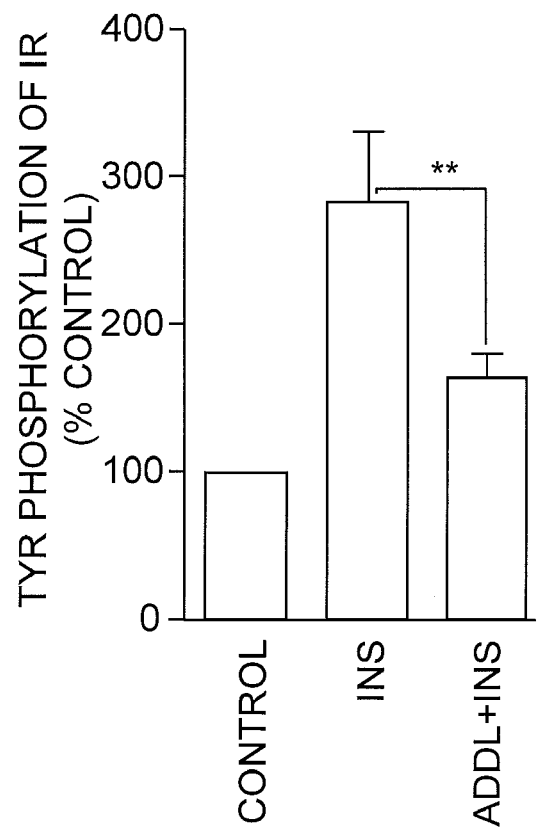

FIG. 5 shows ADDL-induced insulin receptor impairment. Rat primary hippocampal (FIG. 5A) and cortical (FIG. 5B) neuronal cultures were treated with 50 nM oligomeric Aβ peptide assemblies (ADDLs) in the presence or absence of 100 nM insulin (INS) at 37° C. for 1 hour. The tyrosine phosphorylation extent of insulin receptor was examined by precipitating insulin receptor with anti-insulin receptor antibody followed by blotting with anti-pTyr antibody on western blots. The INS-induced Tyr phosphorylation of the receptor was significantly inhibited (**p<0.01).

Figure 6:
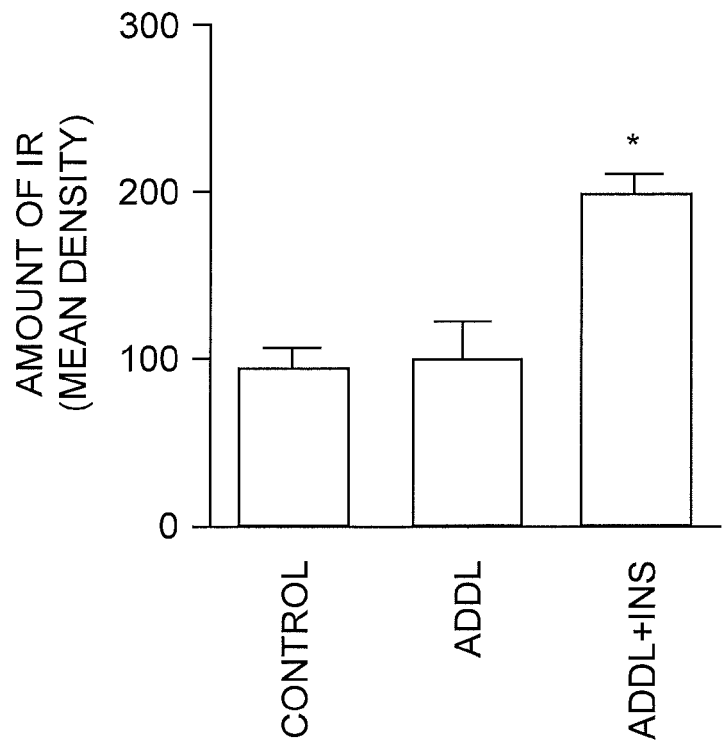

FIG. 6 demonstrates that insulin treatment increases ADDL/insulin receptor interaction. NIH3T3 cells overexpressing the insulin receptor were respectively treated with ADDLs and ADDLs+insulin. Cells were subjected to precipitation by an anti-ADDL antibody, followed by detection of insulin receptor from the precipitated proteins. Activation of insulin receptor resulted in significant increases in ADDL-insulin receptor complex.

Figure 7:
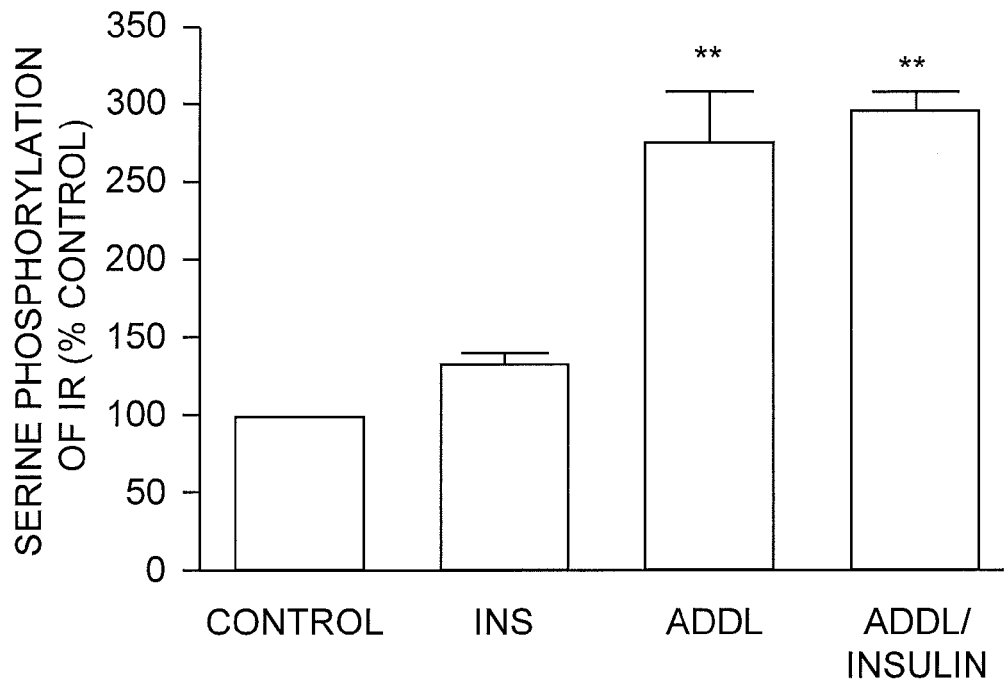

FIG. 7 shows ADDL-induced serine phosphorylation in hippocampal insulin receptors. Cultured rat hippocampal neurons were treated with 150 nM ADDLs at 37° C. for 60 minutes in the presence or absence of 100 nM insulin. The cell lysates were subjected to immunoprecipitation using an anti-insulin receptor antibody. The precipitated insulin receptors were analyzed by western blot with an anti-phosphoserine antibody to detect the serine phosphorylation extent of insulin receptor (pSer-IR). The pSer-IR extent was normalized with the total amount of precipitated insulin receptor. Each condition was converted to percent control before analyzed one-way ANOVA, **p<0.01.

Figure 8:
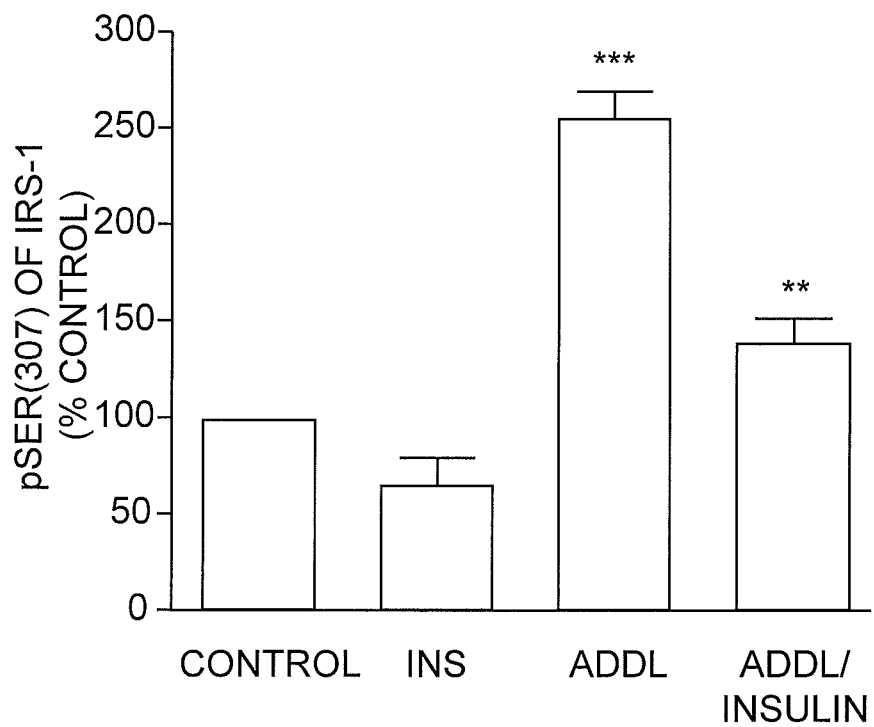

FIG. 8 shows an ADDL-induced increase in IRS1 serine307 phosphorylation. Hippocampal neuronal cultures were incubated with 150 nM ADDLs at 37° C. for 60 minutes in the presence or absence of 100 nM insulin. Equal amount of total proteins from soluble cell lysates from each condition was separated on SDS-PAGE and transferred to nitrocellulose membranes. The phosphorylation extent of IRS1 Ser307 was detected with an anti-IRS1 PSer307 antibody. Identical samples on a separate membrane were blotted with an anti-total amount of IRS1 (rIRS1). The immunoreactivities of pIRS1(Ser307) were normalized with those of rIRS1. Values from each experimental group were converted to percent control and analyzed with one-way ANOVA, *p<0.0001; p<0.01.

FIG. 9 shows ADDL-induced enhancement in phosphorylation of Akt ser473. Hippocampal and cortical neuronal cultures were treated with 150 nM ADDLs in the presence or absence of insulin for 1 hour or 6 hours. To inhibit PP2A activity, cells were pretreated with 10-50 nM okadaic acid before incubation with insulin. Equalized total amount of protein from soluble cell lysates were separated on SDS-PAGE, and pAkt ser473 detected on western blots with a specific antibody against pAkt ser473. Identical samples transferred to a separate membrane were detected with an anti-total Akt (rAkt) antibody for internal normalization. The normalized pAkt extent from each experimental condition was converted to percent control and analyzed with one-way ANOVA, **P<0.01.

Figure 10:
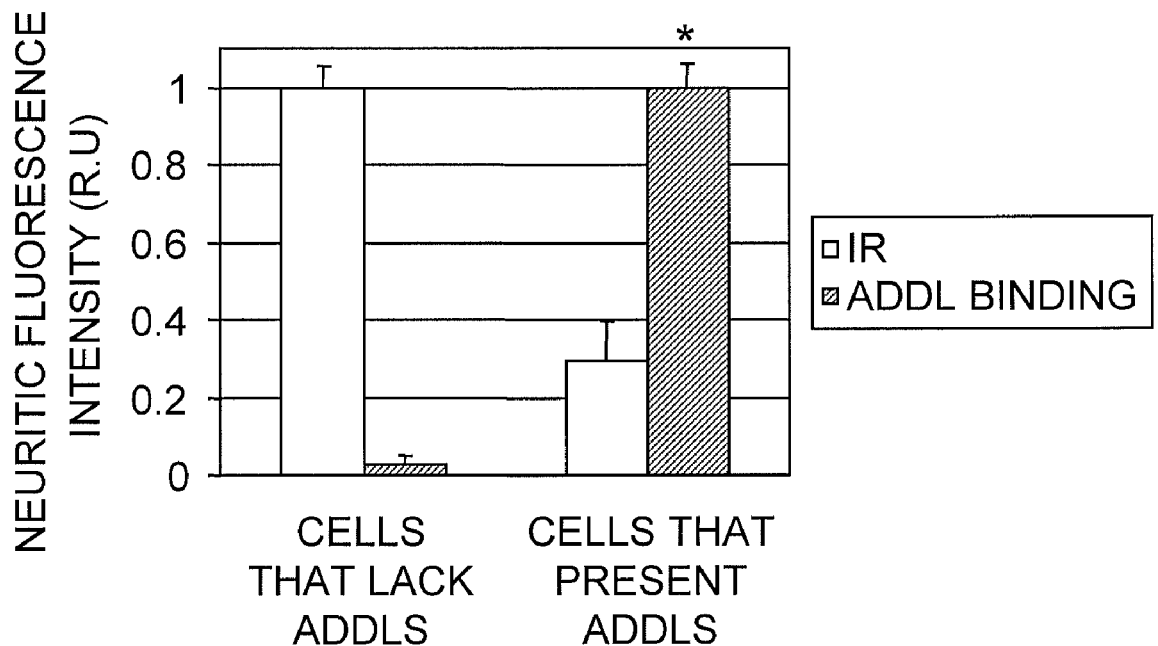

FIG. 10 shows quantification of dendritic IRα fluorescent intensity following ADDL treatment.

Figure 11:
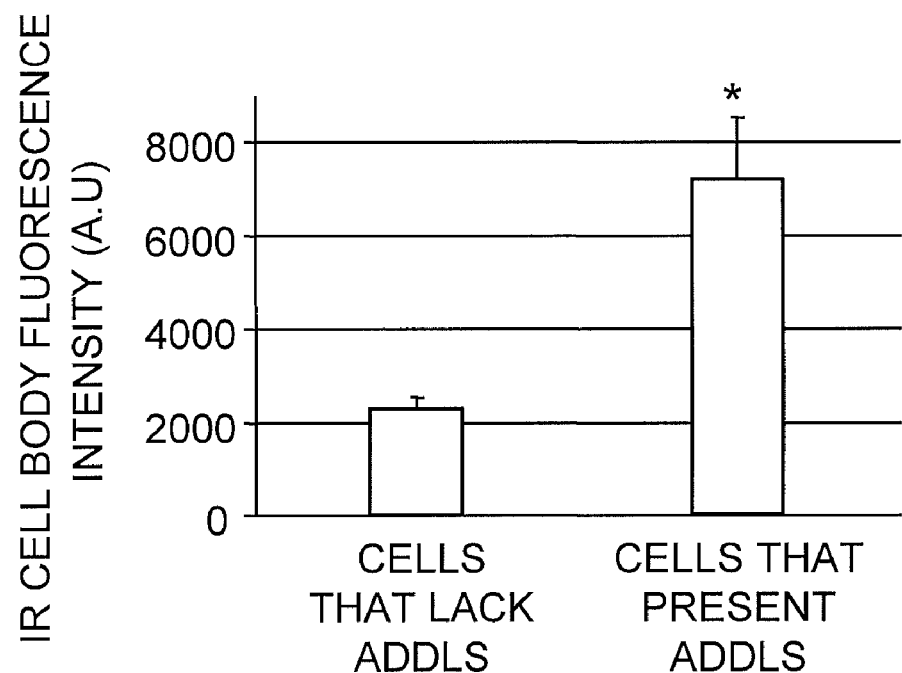

FIG. 11 shows insulin receptor immunoreactivity in cell bodies of cells treated with ADDLs and ADDL-free cells.

DETAILED DESCRIPTION OF THE INVENTION

A breakthrough in recent Alzheimer's disease (AD) research is the identification of neurotoxic, soluble, amyloid β peptide assemblies, also known as ADDLs or ADDL-related assemblies, as the major molecular agent responsible for the synaptic failure and degeneration that underlie memory deficits in early AD. The CNS insulin receptor (IR) plays an important role in modulation of synaptic transmission, cognition, and neuronal survival. Also, IR impairment in type II insulin resistant diabetes is linked to a high risk of AD development. Disclosed herein is data showing that soluble oligomeric Aβ peptide assemblies attack IR signaling in cultured neurons and cause insulin resistance.

Soluble oligomeric Aβ peptide assemblies have now been found to bind activated IR in an in vitro assay, with binding colocalized partly with neuronal IR along dendrites. Treatment of rat primary hippocampal cell cultures with a low concentration (100-150 nM) of soluble oligomeric Aβ peptide assemblies caused a significant inhibition of insulin-stimulated IR tyrosine phosphorylation, indicating a reduction in IR kinase activity. The inhibition was more severe under neuronal depolarization and glutamate stimulation and could be rescued by chelation of intracellular $Ca^{2+}$ with BAPTA-AM (1,2-bis(o-aminophenoxy)ethane-N,N,N',N'-tetraacetic acid tetra(acetoxymethyl)ester). This indicates that soluble oligomeric Aβ peptide assembly-inhibited IR activity may be associated with excessive intracellular $Ca^{2+}$ resulting from hyperactive excitatory neuronal transmission and glutamate receptor activities.

Furthermore, insulin-induced MAP kinase phosphorylation was significantly inhibited. The soluble oligomeric Aβ peptide assembly-induced insulin resistance changes were also detected downstream in molecules of the IR signaling pathway. For example, ADDL treatment caused a significant increase in serine307 phosphorylation of insulin substrate-1 (IRS-1) and insulin-induced phospho-Akt (serine-473). Both phospho-IRS1 (ser307) and phospho-Akt(473) play negative regulatory roles to IR kinase activity within a signaling feedback loop, and their enhancement marks insulin resistant metabolic disorders. The fact that soluble oligomeric Aβ peptide assemblies cause enhanced serine phosphorylation in these molecules indicates that soluble oligomeric Aβ peptide assemblies interfere with functions of IR signaling leading to CNS insulin resistance. Given that the IR plays important roles in synaptic modulation and neuronal survival, it is contemplated that soluble oligomeric Aβ peptide assembly-induced CNS insulin resistance contributes to AD-associated synaptic/neuronal degeneration. Moreover, it has also been found that an intact IR activity is essential for preventing soluble oligomeric Aβ peptide assembly accumulation. Thus, a compromised CNS IR function due to soluble oligomeric Aβ peptide assembly-induced insulin resistance can result in abnormal Aβ metabolism/catabolism leading to ADDL formation/aggregation. Identified herein is a signaling loop in which molecular pathology of AD and type II diabetes can be interconnected.

In this regard, the present invention is a novel strategy for regulating the activity of soluble oligomeric Aβ peptide assemblies based on the unexpected observations that insulin treatment stimulates the rapid uptake and clearance of soluble oligomeric Aβ peptide assemblies from cell-culture media surrounding both neuronal and non-neuronal cells. This process is blocked by an insulin receptor kinase inhibitor and appears to operate by a pathway distinct from the synaptic, memory-compromising effects of soluble oligomeric Aβ peptide assemblies on a specific sub-population of hippocampal neurons. It is contemplated that soluble oligomeric Aβ peptide assembly uptake can be enhanced by small molecules, e.g., insulin, insulin analogs, or insulin-like molecules, via activation of known or novel insulin-sensitizing pathways, and that these ADDL uptake enhancers (AUEs) can represent new and effective therapeutics.

Therefore the present invention provides a method for enhancing the cellular uptake of soluble amyloid beta oligomers by contacting a cell (e.g., a neuronal or non-neuronal cell) which expresses an insulin receptor with an agent that enhances insulin receptor signaling and cell-based primary screening assays to identify ADDL uptake enhancers (AUEs). Methods for validating these primary screening assays using positive and negative control compounds and conditions are also provided.

Detailed objectives of the present invention include, but are not limited to, primary screening assays in neuronal and glial cell lines to identify AUEs and the validation of primary screening assay via control compounds such as known insulin signaling and receptor antagonists and insulin sensitizers. Screening assays of the invention are based upon soluble oligomeric Aβ peptide assembly uptake in primary hippocampal cultures as compared to other neuronal and glial cell lines, wherein enhanced cellular uptake is indicative of an agent which is useful for enhancing cellular uptake of soluble oligomeric Aβ peptide assemblies. Assays of the invention can be carried out on a small scale or in 384-well automated high-throughput mode. Alternate assay formats include sensitive quantification of soluble oligomeric Aβ peptide assembly levels in culture medium or environment surrounding the cells.

Compounds which can be screened in accordance with the present invention include insulin, insulin analogs (e.g., Lispro insulin, Aspart insulin, Glulisine insulin, Glargine insulin or Detemir insulin), or insulin-like molecules; as well as libraries of pure agents such as proteins, polypeptides, peptides, nucleic acids, oligonucleotides, carbohydrates, lipids, synthetic or semi-synthetic chemicals, and purified natural products; and libraries of agent mixtures such as extracts of prokaryotic or eukaryotic cells and tissues, as well as fermentation broths and cell or tissue culture supernates.

The invention disclosed herein further includes: screening of compound libraries to finalize high-throughput screening (HTS) parameters; HTS of diverse libraries containing numerous lead-like compounds; configuration of secondary assays to validate and characterize screening hits; synthesis of focused combinatorial libraries to establish structure-activity relationships for validated screening hits; multiple parallel synthesis and/or medicinal chemistry to transform validated hits into optimized lead compounds; confirmation of lead compound mode of action in tertiary biological assays; and evaluation of promising lead compounds in selected animal models to demonstrate AUE efficacy.

The results disclosed herein indicate that memory malfunction is the direct and immediate consequence of soluble oligomeric Aβ peptide assembly binding to synaptic receptors. At the earliest times, low concentration soluble oligomeric Aβ peptide assemblies would elicit subtle memory deficits, while progressively higher concentrations would trigger more severe deficits. Beyond the immediate signaling malfunction in otherwise healthy neurons, persistent soluble oligomeric Aβ peptide assembly attack would also trigger unabated transcriptional activity, leading to accumulating cellular damage (e.g., tau phosphorylation) and ultimately cell death.

Insulin treatment results in a substantial reduction of extracellular soluble oligomeric Aβ peptide assemblies, while inhibition of tyrosine kinase activity of the insulin receptor results in elevated extracellular soluble oligomeric Aβ peptide assembly levels. Interestingly, it also appears that soluble oligomeric Aβ peptide assemblies themselves can inhibit insulin receptor signaling, which sets up a scenario whereby increasing soluble oligomeric Aβ peptide assembly levels can become increasingly effective at blocking their own cellular uptake and clearance. The presence of soluble oligomeric Aβ peptide assemblies in the brain can also set up a rather sinister scenario whereby soluble oligomeric Aβ peptide assemblies trigger insulin insensitivity and whereby insulin insensitivity arising from other factors contributes to increased levels of extracellular soluble oligomeric Aβ peptide assemblies. There is mounting clinical evidence that AD and insulin-resistant diabetes (NIDD) may be linked (see e.g., Arvanitakis, et al. (2004) *Arch. Neurol.* 61(5):661-6). Also, a recent study demonstrated that diet-induced insulin resistance brought about an increase in Aβ levels in Tg2576 AD mice (see e.g., Ho, et al. (2004) *FASEB J.* 18(7):902-4). This was attributed to an increase in γ-secretase activity or a possible reduction in Aβ degradation by insulin-degrading enzyme (IDE). In view of the observations of soluble oligomeric Aβ peptide assembly uptake disclosed here, it is contemplated that reduced cellular clearance of soluble oligomeric Aβ peptide assemblies can also contribute to elevated Aβ levels. More severe memory deficits are expected to result from elevated soluble oligomeric Aβ peptide assembly concentrations, with incremental increases in Aβ monomer contributing only to the extent that increased soluble oligomeric Aβ peptide assemblies form.

The observation of insulin-stimulated soluble oligomeric Aβ peptide assembly uptake indicates that insulin-sensitizing drugs, such as metformin or the PPARγ agonists, will exert a similar effect in circumstances where insulin signaling is compromised. Metformin appears to enhance the tyrosine kinase activity of the insulin receptor by interacting with its intracellular domain (see e.g., Stith, et al. (1998) *Biochem. Pharmacol.* 55(4):533-6), while PPARγ agonists (e.g., rosiglitizone and pioglitzone) can act through multiple pathways including upregulation of adiponectin and the glucose transporter GLUT4, and down-regulation of TNFα, which compromises insulin receptor signaling. A number of papers have discussed possible protective roles for PPARγ agonists in Alzheimer's disease based on their ability to down-regulate inflammatory cytokines such as IL-1b, IL-6, and TNFα, however, a recent study has demonstrated that rosiglitizone and pioglitizone activate rapid and efficient clearance of exogenously added Aβ from the media in a variety of cell types transfected with PPARγ (see e.g., Camacho, et al. (2004) *J. Neurosci.* 24(48):10908-17). Therein it was demonstrated that Aβ production was not reduced, and it was indicated that no change in intracellular Aβ levels could be detected. As a result, it was postulated that increased degradation was responsible, in spite of the inability to demonstrate any involvement of known degrading enzymes. This study only used the standard anti-Aβ antibodies, rather than antibodies specific for soluble oligomeric Aβ peptide assemblies, so it is possible that internalized soluble oligomeric Aβ peptide assemblies may not have been detected.

PPARγ agonists are widely prescribed for NIDD, however, a growing list of side effects limits broader utility. These include weight gain due to increased fat uptake by adipocytes, pulmonary edema (see e.g., Nesto, et al. (2004) *Diabetes Care* 27(1):256-63), increased heart failure (see e.g., Marceille, et al. (2004) *Pharmacotherapy* 24(10):1317-22), and decreased bone mineral density (see e.g., Soroceanu, et al. (2004) *J. Endocrinol.* 183(1):203-16). The broad spectrum of side effects undoubtedly stems from the fact that PPARγ is widely expressed, with its wide-ranging activities dependent upon the tissues in which it is expressed. It is likely that the insulin signaling benefits of PPARγ agonists are mediated by a limited subset of PPARγ-processes, and it is possible that enhanced soluble oligomeric Aβ peptide assembly uptake is mediated by processes or signaling molecules downstream of PPARγ. Because these processes or molecules remain unidentified, it is believed that cell based screening assays involving specific quantification of extracellular soluble oligomeric Aβ peptide assemblies constitute an optimum strategy for discovery of soluble oligomeric Aβ peptide assembly uptake enhancers with novel modes of action.

A possible mechanistic hypothesis for AD is that soluble oligomeric Aβ peptide assemblies trigger synaptic dysfunction, leading first to subtle cognitive deficits (e.g., MCI), with prolonged exposure causing the more severe deficits and accumulated neuronal pathology characteristic of AD. Accordingly, therapeutics acting directly on soluble oligomeric Aβ peptide assemblies or on soluble oligomeric Aβ peptide assembly-activated processes should block and even reverse disease symptoms.

Therefore, particular embodiments of this invention also embrace the use of insulin, as well as other agents that enhance insulin receptor signaling, in the treatment of a disease associated with soluble Aβ peptide assemblies. Such diseases include, but are not limited to, Alzheimer's disease, Down's syndrome, mild cognitive impairment, stroke-associated dementia, and the like, in which compromised nerve cell function is linked to the formation and/or the activity of soluble oligomeric Aβ peptide assemblies, also known as ADDLs, and ADDL-related assemblies.

Treatment involves administering to a subject in need of treatment an effective amount of an agent (e.g., insulin) that enhances cellular uptake of soluble amyloid beta oligomers in the brain of the subject thereby treating the disease associated with soluble Aβ oligomers. In most cases the subject being treated will be a human being, but treatment of agricultural animals, e.g., livestock and poultry, and companion animals, e.g., dogs, cats and horses, is expressly covered herein. The selection of the dosage or effective amount of an agent is that which has the desired outcome of preventing, reducing or reversing at least one sign or symptom of the disease or disorder being treated.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of an agent at levels lower than that required in order to achieve the desired therapeutic effect and gradually increase the dosage until the desired effect is achieved. This is considered to be within the skill of the artisan and one can review the existing literature on a specific compound or similar agents to determine optimal dosing.

EXAMPLE 1

Figure 1:
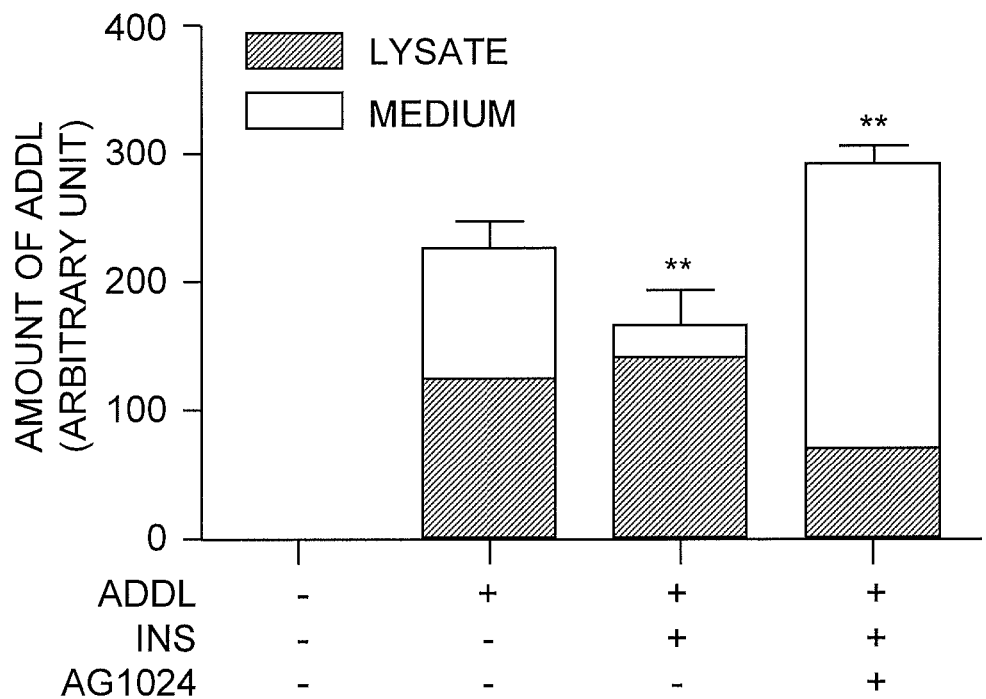
FIG. 1 shows the effects of insulin on soluble oligomeric Aβ peptide assembly uptake. Serum-deprived insulin receptor overexpressing cells were incubated with 100 nM of oligomeric Aβ peptide assemblies in the presence or absence of 100 nM insulin. To inhibit insulin receptor tyrosine kinase, tryphostin AG1024 was preincubated with cells for 45 minutes before oligomeric Aβ peptide assembly and insulin application. The amount of oligomeric Aβ peptide assemblies present in cell lysates and culture medium is presented.

ADDL Uptake and Clearance by Non-Neuronal Cells Occurs Via Signaling of the Insulin Receptor To establish the roles of insulin receptor in neurotoxic soluble oligomeric Aβ peptide assembly (referred to hereafter as ADDL) clearance and trafficking, experiments were performed to determine the extra- and intracellular levels of ADDLs added to cells over-expressing insulin receptor. The cells were incubated with 100 nM ADDL with or without insulin. The results of this analysis indicated that insulin treatment stimulated ADDL uptake: an increase in ADDL levels from the cell lysates was accompanied by a decrease in ADDL levels from the extracellular medium (FIG. 1). As a result, the total amount of ADDLs was significantly reduced (P<0.01). When cells were pretreated with the insulin receptor kinase inhibitor AG1024, the insulin-stimulated ADDL internalization was prevented, resulting in a markedly higher amount of ADDL aggregates in the extracellular medium. Total ADDL levels were higher than other treatment conditions. ADDLs bind to the membrane of the insulin receptor over-expressing cells. In the presence of insulin, ADDLs were internalized and detected in the center of the intracellular compartment. In the presence of AG1024, the majority of ADDLs were retained in the extracellular compartment.

Figure 2A:
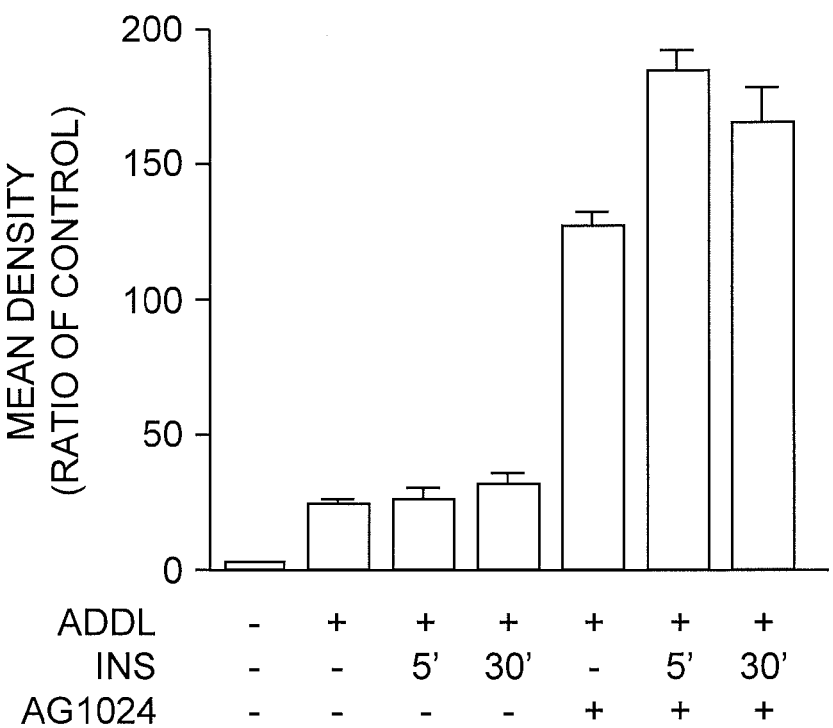
FIG. 2 shows the effects of insulin and insulin receptor inhibitor(s) on levels of extracellular soluble oligomeric Aβ peptide assemblies. Primary cortical cultures were prepared from 1-day old pups and maintained in serum-free neurobasal A medium complemented with 2% B-27, 05 mM L-glutamine and 5 µg/mL bFGF. Synthetic oligomeric Aβ peptide assemblies (100 nM) were applied to cultured cortical neurons and incubated at 37° C. for 30 minutes. Insulin (100 nM was added to cultures either together with the oligomeric Aβ peptide assemblies or 30 minutes after oligomeric Aβ peptide assembly addition and incubated with cells for 5 minutes. To inhibit the insulin receptor, AG1024 was included in the culture prior to oligomeric Aβ peptide assembly treatment. Upon termination of the reaction, the extracellular medium was collected and concentrated by centrifugation. After resolution on SDS-PAGE, oligomeric Aβ peptide assemblies were detected with 6E10 antibody and levels measured via densitometry scan (FIG. 2A). Cell lysates were also immunoprecipitated with 6E10 antibody (FIG. 2B). After separation on SDS-PAGE, the precipitated oligomeric Aβ peptide assemblies were detected on western blots with 6E10 antibody. The bar graph (mean±SE) summarizes data from four independent replicated treatments.
Figure 2B:
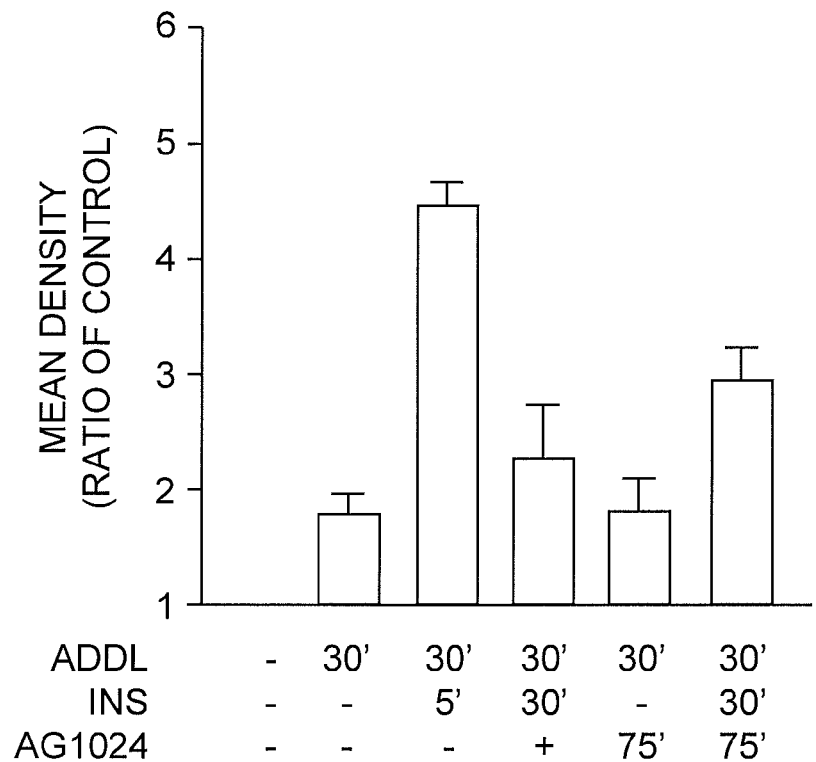

ADDL Uptake and Clearance by Neurons Occurs Via Insulin Receptor Signaling. Insulin-stimulated ADDL uptake was also observed in cultured cortical and hippocampal neuronal cells prepared from 1-day old pups. Cells were treated with 100 nM synthetic ADDLs in the presence or absence of insulin. Extracellular ADDL levels were measured on western blots using a concentrated medium. As shown in FIG. 2A, a substantial amount of ADDLs was detected in the extracellular medium after incubated with cortical cultures at 37° C. for 30 minutes. Again, inhibition of insulin receptor kinase activity by tyrphostin AG1024 caused striking aggregation of ADDLS in the extracellular medium. On the other hand, the intracellular ADDLs were detected by immunoprecipitation (FIG. 2B). Insulin caused an increase of ADDL oligomers in the cell lysate fractions (FIG. 2B, lane 3), indicating enhanced binding or uptake. This uptake, however, was prevented by GA1024 (FIG. 2B, lane 5, 6).

Similarly, insulin treatment reduced aggregated ADDLs in the extracellular medium in a dose-response manner, and stimulated a striking ADDL uptake into hippocampal neurons in a clear dose-response manner. These results indicate that the binding and/or internalization of ADDLs into hippocampal neurons are more sensitive to insulin stimulation. Immunofluorescent staining showed a consistent insulin-stimulated ADDL internalization. These results indicate that the binding and internalization of ADDLs into the hippocampal are more sensitive to insulin stimulation.

Enhanced ADDL Uptake and Clearance is Toxic to Neurons. To test whether insulin induced ADDLs are toxic to neurons, MTT assays were performed to measure cell viability after the ADDL/insulin treatment. As shown by FIG. 3, there were no apparent toxic effects when hippocampal neurons were treated with ADDLs/insulin for 4 hours.

ADDLs Inhibit Insulin Receptor Signaling. To assess effects of ADDLs on insulin receptor activity, tyrosine phosphorylation of insulin receptor β subunits from hippocampal neuronal cultures were measured after the ADDL treatment in the presence and absence of insulin. ADDL treatment resulted in an increase in tyrosine phosphorylation of the insulin receptor accompanied by a reduction in the amount of the insulin receptor. Insulin alone also stimulated an increase in tyrosine phosphorylation of the insulin receptor (FIG. 4). However, when insulin was added to the ADDL-treated neurons, the phosphorylation of the insulin receptor was inhibited. While the mechanism for ADDL alone-induced phosphorylation of the insulin receptor remains to be understood, ADDL treatment clearly abolished insulin-stimulated receptor tyrosine phosphorylation.

Development of High-Throughput Fluorescence-Based ADDL Quantification Assays to Detect Small Molecule ADDL Uptake Enhancers. The development of high throughput assays for the detection of small molecule ADDL uptake enhancers is greatly facilitated by leveraging pre-existing assay technology for sensitive detection of ADDL levels. High-throughput, fluorescence-based, ADDL quantification screening assays have been developed that are routinely used in small molecule anti-ADDL therapeutic discovery programs. Critical to this progress has been the development of ADDL-selective antibodies, such as mAb ACU-AS, which have little or no Aβ monomer affinity. Advantageously, ACU-AS4 recognizes trimers, tetramers, and 12-24-mers that assemble from the trimers and tetramers.

High-throughput format binding assays have been developed for detection of physiological levels of ADDLs using streptavidin-lanthamide conjugate and time-resolved fluorescence detection. These assays have proven to be sufficiently sensitive to detect ADDL levels at physiologically relevant ADDL concentrations (e.g., 1-10 nM). These assays can be optimized to detect levels of biotinylated ADDLs in supernatants and cell lysates from neuronal and non-neuronal cultures. Alternative approaches can involve the incorporation of antibodies such as ACU-AS4 into a sandwich ELISA format. The use of engineered cells over-expressing insulin receptor can also further increase sensitivity of the assay.

These assays are validated via the use of control compounds such as insulin signaling and receptor antagonists and insulin sensitizers. The effects of insulin signaling blockers that were intended to be used for compound screenings on insulin receptor activity were tested. Both erythrosin B (EB), an insulin binding blocker, and tyrphostin AG1024, an insulin kinase activity blocker, significantly inhibited the insulin-stimulated insulin receptor phosphorylation. Because these compounds block insulin signaling at different steps of the molecular cascade, they can serve as candidates for screening antagonists for insulin-induced ADDL uptake. More importantly, the effects of insulin receptor sensitizers on ADDL uptake and clearance can be tested.

Experimental Design and Methods. The indication that ADDL uptake can be enhanced by small molecules via activation of known or novel insulin-sensitizing pathways, and that these ADDL uptake enhancers (AUEs) can represent new and effective anti-ADDL therapeutics that will prevent ADDL-induced cognitive deficits and slow or reverse disease progression in humans, serves as the framework for the studies disclosed herein. Initially, the studies (i) confirm and extend preliminary observations of stimulated ADDL uptake in neuronal and glial cell lines, (ii) establish prototype cell-based primary screening assays to identify ADDL uptake enhancers (AUEs), and (iii) validate a primary screening assay using positive and negative control compounds and conditions.

Primary Screening Assays in Neuronal and Glial Cell Lines to Identify AUEs. Such screening assays include the analysis of ADDL uptake in neuronal and glial cell lines by comparison to responses in primary hippocampal cultures. It is believed that insulin-induced ADDL uptake to neuronal and glial cells will have a different impact on ADDL clearance and neuronal survival. Therefore, the effects of insulin-stimulated ADDL uptake in primary neuronal and glial cultures are measured and differentiated.

Primary neuronal cultures from embryonic brains can be prepared and maintained in neurobasal medium complemented with B27. Cells can be cultured in 96-well plates and changed to fresh neurobasal medium approximately 4 hours prior to ADDL treatment. ADDLs prepared according to standard protocols at sub-micromolar concentrations can be applied to neurons and incubated at 37° C. for 1 hour. Different doses of insulin ranging from 0 nM, 1 nM, 10 nM, 100 nM, 500 nM, to 1 μM can be added to and allowed to react with ADDL-treated cells at 37° C. for 5 minutes. To block insulin/insulin receptor activation, an insulin receptor kinase inhibitor AG1024 or an insulin binding antagonist such as (erythrosin B) can be applied to cells 45 minutes before ADDL treatment. Upon termination of the reaction, the extracellular medium from all groups can be rapidly collected into microtubes and added with protease inhibitor cocktails (SIGMA, St. Louis, Mo.) to a final concentration of 1%. The medium samples can be spun at 1,000×g for 5 minutes and the supernatants subjected to ELISA using an oligomer-specific antibody to quantify the extracellular ADDL concentration. The remaining cells can be rapidly rinsed with PBS twice and fixed with 4% formaldehyde made in PBS pH 7.4 at room temperature for 10 minutes. After washes with PBS, the cells can be used to quantify the bound and/or internalized ADDLs using ELISA methodology.

To measure the insulin-induced ADDL uptake in glial cells, the astrocytic glial cells can be prepared from the brain of 1-day old postnatal pups. Upon complete removal of neurons, the astrocytes can be frozen and used for multiple splits. The astrocytes can be cultured in 96-well plates to approximately 85% confluence and serum-"starved" overnight to synchronize the cell division cycles prior to the experimental treatment. The same treatment of ADDL, insulin and pharmacological reagents as well as the subsequent ELISA quantification can be applied to glial cells as to the neuronal cultures described above.

Data obtained from different experimental groups can be subjected to appropriate statistical analyses such as the t-test and one/two-way ANOVA depending on the experimental designs. The analyses can be performed using standard computer software such as GRAPHPAD, PRISM, or SPSS.

Alternate Assay Formats for Sensitive Quantification of ADDL Levels in Cell Line Supernatants. Since the preparation of primary neuronal and glial cultures can be costly and technically demanding, the suitability of immortalized tumor cell lines derived from brain neuronal and glial cells as substitute models can be tested. The neuroblastoma N2A cells and glioma HTB-138 cells can be cultured in high glucose DMEM containing 10% FBS. Although N2A cells have been known to express reasonable abundance of the insulin receptor, the level of insulin receptor in these cell lines by western blotting can be verified. Subsequently, N2A and HTB cells can be serum "starved" overnight prior to the experimental treatment. The cells can be treated with ADDLs followed by different doses of insulin in the presence or absence of insulin receptor inhibitors. ADDLs from the extracellular medium and the cell lysates supernatant can be measured using ELISA as described herein. These data can be used to assess ADDLs uptake and clearance in N2A and HTB cells, which can also be compared to the results from primary neuronal and glial cultures. Furthermore, whether the quantitation sensitivity can be augmented by increasing the abundance of insulin receptor by stable gene transfection can be tested. The full length of human insulin receptor can be constructed to the pcDNA™3.1 (+) vector (INVITROGEN) and transfected into N2A and HTB cells using LIPOFECTIN (INVITROGEN) reagents. Cells can be selected with G418 (800 ug/ml) to generate stable cell lines according to published protocols (He, et al. (1999) *Proc. Natl. Acad. Sci. USA* 96(11):6495-500). In addition, the brain form of insulin receptor (an alternative splicing variant lacking exon 11) construct can also be generated and stably transfected into N2A and HTB cells. The insulin receptor overexpressing N2A and HTB cells can be treated with ADDLs and insulin as above. The amount of ADDLs in the extracellular medium can be measured with ELISA as described above. Results from insulin receptor overexpressing cells can be compared to those from wild type N2A and HTB cells, as well as to those from primary neuronal and glial cultures. Successful establishment of the insulin receptor-overexpressing immortalized brain derived cell lines is expected to provide a stable and robust cell-based model for the future high-throughput screen based on the ADDL-IR interaction.

The same methods as described above can be applied to data analyses in these studies.

Assay Parameters and Screening Performance in 384-Well Automated High Throughput Mode. Comparison of quantitative methods for the extracellular ADDL concentrations (dot, western blots, ELISA): The extracellular ADDL concentration can be used as a primary parameter for ADDL uptake and clearance, and the most sensitive and feasible method for high-throughput screening can be developed. Extracellular medium from ADDL-treated cells in the presence or absence of insulin can be collected. After adding a protease inhibitor cocktail (final concentration 1%) and centrifugation at 1,000×g for 5 minutes to remove any contained cells, the extracellular medium can be concentrated using spin filters with an appropriate pore size. The concentrated ADDL medium can be measured by 1) dot blotting, 2) western blotting transferred from SDS-PAGE, and 3) ELISAs. Data from each method can be quantified and compared with statistical analyses described in the sections above. Furthermore, quantification of ADDLs from concentrated extracellular medium can be evaluated using 384-well automated system to develop the most efficient and rigorous measurement.

Quantitative Methods for the Intracellular ADDL Concentration from Soluble and Insoluble Fractions. While the extracellular medium can be used as the primary material for measurement of ADDL uptake, it is also useful to measure ADDL levels from cell lysates. It has been found that immunoprecipitation is an excellent method to detect intracellular (soluble or bound) ADDLs. However, when separated on SDS-PAGE, the IgG heavy and light chains from the primary antibody could mask certain order ADDL species such as 12mer that has a similar mobility to the IgG chain. To overcome this, immobilized anti-ADDL IgGs can be produced by crosslinking ADDL-specific antibody(s) to SEPHADEX beads, which can be denaturing resistant during the SDS-PAGE sample treatment process. Cultured cells can be treated with ADDL in the presence or absence of insulin. After removal of the extracellular medium, cell lysates can be prepared in a lysis buffer containing 10 mM Tris-HCl, pH 7.4, 150 mM NaCl, 1 mM EDTA, 1 mM EGTA 1% TRITON X-100, 0.5% NP40, and 1% protease and tyrosine phosphatase inhibitor cocktails. The soluble and insoluble fractions can be separated by centrifugation, ADDL from both of which can be measured using similar methods described above.

ADDL levels from the extracellular medium and intracellular fractions can be summed as parameters for estimation of ADDL clearance. The ratio of intracellular over extracellular (or the total) ADDL levels can be used as parameters to assess ADDL uptake. Data from different treatments can be analyzed for statistical significance using computer software (GRAPHPAD, PRISM, or SPSS).

Primary Screening Assays Via Control Compounds. In some embodiments, assays are performed using known insulin signaling and receptor antagonists and insulin sensitizers. With sensitive cell models and optimized assay parameters established in the above section, these studies can be aimed to alter ADDL uptake using known insulin signaling sensitizers and antagonists.

The peroxisome proliferators-activated receptor (PPAR)-gamma (γ) ligands and agonists have been know to treat insulin resistant type II diabetes by increasing insulin sensitivity. PPAR-gamma is expressed at very low levels in the postnatal and adult brain, but is up-regulated in response to inflammatory stimulations. The PPAR agonists have been show to be neuronal protective against inflammatory factors. Effects of PPAR-gamma agonists on ADDL uptake and clearance can be tested. Several such compounds, including thiazolidinedione (TZD), troglitazone (TGZ), rosiglitazone (RGZ), can be tested. The selected cell model can be treated with ADDL-insulin in the presence of PPAR agonists at optimal doses. The resulting ADDL uptake can be assessed by measuring, respectively, ADDL concentrations from the extracellular and intracellular samples with ELISA. Statistical analyses can be performed used the same computer software as described above.

Cell Viability Assay. Neuro 2A cells (American Type Culture Collection (ATCC) Manassas, Va.) can be plated at optimized concentrations in 96-well plates in 100 μL media. After overnight incubation, cells are rinsed with serum free media containing N2 supplement (INVITROGEN). Vehicle or peptide preparations are added to cells and incubated for 24 and 48 hours at 37° C. in 5% $CO_2$. As taken from the Roche Molecular Biochemicals protocol, the 3-(4,5-dimethylthizaol-2-yl)-2,5diphenyl tetrazolium bromide (MTT) reagent is reconstituted in phosphate-buffered saline to 5 mg/mL. The solubilization solution is 10% SDS in 0.001 M HCl. Ten μl of MTT labeling reagent is added to each well and incubated at 37° C. for 4 hours. One hundred μL solubilization solution is added to each well and the plate is incubated over night at 37°

C. The absorbance of samples is measured at 563 nm. For statistical analysis, an unpaired Student's t-test with unequal variance is used.

Rat Hippocampal Neuronal and Glial Primary Culture. Hippocampal cells can be prepared from E18 embryos and maintained for 21 days in vitro according to known methods (see e.g., Lambert, et al. (2001) *J. Neurochem.* 79(3):595-605). Glial cells can be prepared according to established protocols (see e.g., Zhao, et al. (2004) *J. Neurochem.* 90(3): 609-20). In brief, the dissected cortices are cut into small pieces and digested with papain (1 mg/ml). Cell suspensions are produced and seeded in uncoated 25 cm$^2$ flasks and cultured with high glucose DMEM containing 10% FBS. The culture medium is changed after 6-8 hours to remove unattached cells including neurons, which are not able to attach to a non-poly-L-lysine-coated plastic surface. Two to three medium changes are applied to cells every two days, which is meant to yield cultures consisting of >95% type I astrocytes as characterized by glial fibrillary acidic protein (GFAP) immunoreactivity.

Cultures of N2A and HTB Cell Lines. N2A and HTB cells can be cultured and maintained in high glucose DMEM containing 10% FBS. The medium can be changed every 3-4 days and cells passaged when confluency is achieved. For ADDL and pharmacological treatment, cells are cultured to approximately 80% confluence and subjected to serum deprivation at least 12 hours prior to the experiment.

ADDL preparations. Aβ 1-42 peptide can be obtained from American Peptide, with lot-choice contingent upon quality control analysis. Quality control of ADDL preparations consists of SDS-immunoblots to confirm structure and MTT assay to confirm toxicity. ADDLs can be made using known methods (see e.g., Klein, et al. (2004) *Neurobiol. Aging.* 25(5):569-80).

ADDL Antibodies. Mouse monoclonal antibodies can be generated by ADDL vaccination in collaboration with an outside contractor, Immuno-Precise Antibodies Ltd. (Victoria, Canada). Additional antibodies can be generated. ADDL-selective antibodies can be characterized as described herein. Key properties are high-affinity recognition of assembled oligomeric forms of Aβ 1-42, but not monomer or fibrils.

Fractionation of ADDL Oligomers/Gel Filtration by HPLC. Oligomers can be fractionated by size using an AKTA EXPLORER automated liquid chromatography system (Amersham-Pharmacia) fitted with a gel filtration column (SUPERDEX 75 PC 3.2/30, SUPEROSE 12 PC 3.2/30 column for oligomers up to 12-mer, or a SUPERDEX 200 PC 3.2/30 column for larger oligomers). The columns can be calibrated using gel filtration calibration kits available from AMERSHAM. Fractionations can be performed in several different buffer systems, including pH 7.4 borate buffer and pH 7.4 phosphate buffered saline (PBS). F12 cell culture medium can also be used as a mobile phase. The eluate is monitored at 214 nm and 254 nm simultaneously and analyzed by dot blot and western blot (1D and 2D) analyses for oligomeric quantity and species. ADDLs prepared from synthetic Aβ 1-42 peptide can be used as standards.

Preparation of Concentrated Extracellular Medium for ADDL Measurement. Culture media from ADDL and/or pharmacological treated, as well as control cells are collected and mixed with 1% protease cocktail (SIGMA). The media can be concentrated by centrifugation at 20,000×g for 1 hour using CENTRICON (MILLIPORE, 3YM). The concentrated media can be collected and used for ADDL immunoreactive detection.

Preparation of Soluble and Insoluble Cell Lysates. Upon removal of culture medium, cells can be briefly rinsed with 1×PBS and rapidly frozen by placing the plates (or dishes) on dry ice/isopropanol. The plates/dishes can then be removed to water ice and cells added with an appropriate volume of lysis buffer containing 10 mM Tris-HCl, pH 7.4, 150 mM NaCl, 1 mM EDTA, 1 mM EGTA, 1% TRITON X-100, 0.5% NP40, and 1% protease and tyrosine phosphatase inhibitor cocktails. After collection with a cell scrapper, the cell mixture can be lysed on ice for at least 30 minutes with occasional vortex. The lysates can be centrifuged at 10,000 g for 15 minutes. The supernatant and pellet can be collected as soluble and insoluble fractions, respectively.

ELISAS. Biotinylated Aβ 1-42 monomer at 1, 5, 10, 50, 100, 500 and 1000 nM and 0.1 mL assay volume can be incubated in a 96-well streptavidin-coated microplate (biotin binding capacity>20 pmol/well) for 120 minutes at 37° C. Eu$^{3+}$-labeled streptavidin can be added for a final concentration of 100 ng/mL (2 nM) Eu$^{3+}$-SA and 0.2 mL assay volume. After a 15-minute incubation on a plate shaker at 22° C., microplate wells can be washed 5× with 0.2 mL of diluted DELPHIA Wash Concentrate (PERKIN ELMER) and 0.1 mL of DELPHIA Enhancement Solution (PERKIN ELMER) can be added for 15 minutes with shaking prior to measuring Time Resolved Fluorescence (TRF). TRF measurements at 340/612 nm excitation/emission wavelengths can be made using a TECAN GENIOS Pro microplate reader.

Cell Culture. Vertebrate animals can be used for the production of hippocampal cultures for ADDL activity and compound testing. Hippocampal cultures can be produced from embryonic rat pups according to established protocols. For experiments, Sprague Dawley timed pregnant female rats can be euthanized with an overdose of carbon dioxide, followed by decapitation. Research has indicated that these animals experience no discomfort from the euthanization procedure. The E18 pups can be removed and decapitated for dissection of the brain and removal of the hippocampi. Cultures can be generated on a weekly basis using the pups from 2-3 pregnant rats per week and grown for 7-21 days.

To study the effect of ADDLs on synaptic plasticity, it is necessary to use cultures that are widely accepted as a standard model for synaptic formation, maintenance, and replacement. Rat hippocampal cultures have been used for decades as models for synaptogenesis, and the strain conforms to the availability and needed tissue of the research design methods. The generation of cultures on a weekly basis will provide enough material for the investigators to complete all of the necessary experiments.

EXAMPLE 2

ADDL Uptake and Clearance by Neuronal Cells

Soluble Aβ oligomers (ADDLs) play a central role in the development of Alzheimer's disease (AD), during which ADDLs cause damage to synapses that are responsible for cognition impairment and further, neuronal degeneration. New findings disclosed herein indicate that ADDLs attack the insulin receptor signaling system in primary neuronal cultures leading to CNS insulin resistance. Treatment of cultured neurons with ADDLs causes a significant inhibition of insulin-induced insulin receptor activity. The reduced insulin receptor activity is accompanied by increases in serine phosphorylation of insulin receptor, serine (307) phosphorylation of insulin receptor substrate 1 (IRS1), and serine (473) phosphorylation of PKB/Akt. All these serine phosphorylations counter-regulate insulin receptor tyrosine kinase activity. These changes are molecular characteristics of insulin resistance identified in type II diabetes, obesity and hypertension.

Proposed mechanisms underlying ADDL-induced insulin resistance can include: 1) a direct binding of ADDLs to an activated form of insulin receptor; 2) ADDL induced increases in serine phosphorylation of insulin receptor, IRS-1 and Akt via enhancement of excitatory synaptic transmission leading to excessive intracellular $Ca^{2+}$ and $Ca^{2+}$-dependent protein kinases activities such as those of PKC; and 3) ADDL-induced impairment of phosphatase 2A leading to the inhibition of dephosphorylation of serine leading to a left shift of phosphorylation equilibrium (i.e., toward increased serine phosphorylation). Because insulin receptor signaling plays an important role in synaptic plasticity, learning and memory, and neuronal survival, the ADDL-induced CNS insulin resistance can be involved in the mechanism by which ADDLs cause synaptic failure in early stages of AD, and neuronal degeneration and cell death during progression of the disease. Thus, protection of insulin receptor signaling systems, and improving insulin sensitivity can be used as an intervention in AD progression.

Also disclosed herein are findings that indicate that functions of insulin receptors and their signaling molecules are the essential mechanisms in the brain to prevent and/or inhibit ADDL formation. Cells that lack insulin receptor do not have an ability to degrade ADDLs. However, when insulin receptor is expressed, these cells are conferred with a strong capability to break down ADDLs into monomers that are subsequently digested and cleared possibly via activity of specific enzymes whose expression and activity can be enhanced by insulin receptor expression. While inhibition of insulin receptor activity causes ADDLs to be accumulated mainly in the extracellular compartment, inhibition of insulin receptor downstream molecules, such as PI3 kinase and myosin $Mg^{2+}$ ATPase/myosin light chain, results in a marked amount of ADDLs to be retained in the cell membrane compartment. These findings indicate that a possible therapeutic and/or preventive approach of AD can be through the development of protection and/or improvement of insulin receptor signaling pathways in the brain. Because the findings disclosed herein are novel, and no similar reports are found in the literature, the resulting utility can be novel therapeutic and prophylactic treatments of AD.

Since the discovery of ADDLs in the late 90's, evidence has emerged to show that ADDLs are the major molecular pathogen causing synaptic failure responsible for memory impairment in early Alzheimer's disease; and further, for neuronal degeneration leading to cell death during the progression of the disease. At molecular and structural levels, ADDLs bind specifically to dendritic spines where they cause structural damage and downregulation of postsynaptic receptors (such as NMDA receptors) ultimately leading spine loss. The synaptic action of ADDLs correlates well with their potent inhibition in synaptic plasticity such as long-term potentiation, and memory deficits in transgenic mice models. Furthermore, ADDL also result in production of reactive oxygen species and enhance tau phosphorylation suggesting that the actions of ADDLs on neurons are responsible for induction of oxidative stress and neuronal degeneration; both of which are involved in AD molecular pathology. Insulin receptors are abundantly expressed in specific brain regions essential for learning and memory such as cerebral cortex, entorhinal cortex and hippocampus. In respect of neuronal functions, insulin receptor is involved in modulation of synaptic transmission including neurotransmitter release and receptor trafficking. In doing so, insulin receptor signaling may play a role in maintaining the homeostasis of neuronal excitability that is essential for memory processing. Impairments of insulin receptor cause deficits in learning and memory formation, as well as LTP in a disease duration-dependent manner. Insulin receptor signaling also plays an important role in neuronal survival by inactivating pro-apoptotic transcriptional factors and by preventing degenerative changes such as tau hyperphosphorylation. Both cognitive and neuronal survival roles of insulin signaling were mediated via downstream pathways including the IRS-PI3 kinase-PKB/Akt and the Shc/Grb2-Ras-MAP kinase cascade. Upon binding of insulin, insulin receptor undergoes tyrosine phosphorylation that activates the tyrosine kinase activity of the receptor. Subsequently, downstream molecules such as IRS (s) and Shc were recruited to the membrane and bind to the activated insulin receptor, which triggers their tyrosine phosphorylation leading to activation of further down stream molecules. In neurons, it has been generally thought that the IRS-PI3K-Akt pathway is predominantly involved in neuronal survival, whereas the Shc-Ras-MAP kinase pathway is more directly associated with neuronal activities and memory processing. On the other hand, the insulin receptor activity is negatively regulated by its serine phosphorylation catalyzed by PKC, and serine phosphorylation of IRS-1. Phosphorylation of Akt occurs at two sites threonine 308 and serine 473, with the former playing a role in cell survival and the latter counter regulating the insulin receptor activity. Enhanced IRS and Akt serine phosphorylations are found in insulin resistant metabolic disorders (such as type II diabetes) and hypertension. Enhanced Akt serine 473 phosphorylation also was reported in the brain of AD patients. Insulin resistance has been linked to AD etiology due to the facts that the insulin type II diabetes has higher risk for AD development. Dietary-induced insulin resistance causes significantly enhanced Aβ deposit in APP transgenic mice. However, it has now been shown that significant CNS insulin resistance is caused, at least in part, by ADDLs. Given the involvement of insulin signaling in both cognitive functions and neuronal survival, the ADDL-induced CNS insulin resistance may provide a mechanism thereby ADDL cause synaptic failure and neurodegeneration. Thus, the findings disclosed herein have identified one or molecular cascade(s), the protection of which may be used as a therapeutic and/or prophylactic treatment of AD.

Treatment of Primary Neuronal Cultures with ADDLS Results in Inhibition of Insulin-Induced Insulin Receptor Activity. "Synthetic" ADDLs were prepared according to published protocols, and were incubated with hippocampal or cortical neuronal cultures at a final concentration of 50-150 nM for 30 to 60 minutes in the presence or absence of 100 nM insulin. Upon termination of the reaction, the extracellular medium was removed and cell lysates were prepared with a lysis buffer. The tyrosine phosphorylation of insulin receptor was assessed by immunoprecipitation of insulin receptor with a specific anti-insulin receptor antibody, followed by blotting the precipitated receptor with an anti-tyrosine antibody. The results showed that treatment of both hippocampal (FIG. 5A) and cortical (FIG. 5B) neurons with 100 nM insulin resulted in marked increases in insulin receptor tyrosine phosphorylation indicating activation of insulin receptor. However, when ADDLs were present in the cultured cells, the insulin-induced insulin receptor tyrosine phosphorylation was significantly inhibited. The ADDL-induced insulin receptor tyrosine phosphorylation was also seen in the human insulin receptor overexpressed in mouse fibroblast cells (NIH3T3 cells). These results indicate that insulin receptor tyrosine kinase activity is impaired by ADDLs.

ADDLs Bind to Activated Insulin Receptor. This assay assessed whether inhibition of insulin receptor is caused by a direct interaction of ADDLs with the receptor. NIH3T3 cells stably overexpressing the full-length human insulin receptor were treated with ADDLs in the presence or absence of insulin at 37° C. for 60 minutes. The cell lysates were subjected to co-immunoprecipitation, in which a specific anti-ADDL antibody (20C2) was used to precipitated ADDLs and proteins that complexed with ADDLs. This was followed by detection of insulin receptor from precipitated proteins on a western blot. As shown in FIG. 6, a substantially increased amount of insulin receptor was co-precipitated by the anti-ADDL antibody, indicating the interaction of ADDLs with insulin receptor. To test whether the ADDL-insulin receptor interaction is direct, the human insulin receptors from insulin receptor expressing cells with and without insulin treatment were precipitated with an anti-insulin receptor antibody. The precipitated receptors were subjected to ligand blotting assay after resolved on SDS-PAGE and transferred to a nitrocellulose membrane, in which 100 nM ADDLs were incubated with precipitated insulin receptor. The membrane was then washed and blotted with an anti-ADDL antibody to detect binding of ADDLs to insulin receptor. A strong binding of ADDL to insulin receptor was detected only in the activated but not the control insulin receptor.

ADDLs-Cause Insulin Resistance was Correlated with Increases in Serine Phosphorylation pf Insulin Receptor. Results presented herein show ADDL treatment induces an increase in serine phosphorylation of insulin receptor in cultured hippocampal neurons (FIG. 7). Because serine phosphorylation of insulin receptor is known to counter-regulate insulin tyrosine receptor activity, the ADDL-induced serine phosphorylation of insulin receptor can be one of the factors attributed to the ADDL-induced insulin resistance.

ADDLs Induce Insulin Resistance at Levels of Insulin Substrate I (IRS1). The results disclosed herein show that ADDLs induce an increase in serine phosphorylation of IRS-1 at serine 307 residue (PSer307) in cultured hippocampal neurons (FIG. 8). IRS-1 Pser(307) is known to inhibit insulin receptor tyrosine kinase activity and is present in the peripheral insulin resistant disorders. The fact that ADDLs cause increased IRS1 Pser307 indicates that ADDLs induce CNS insulin resistance at multiple levels of the insulin signaling pathway.

Figure 9A:
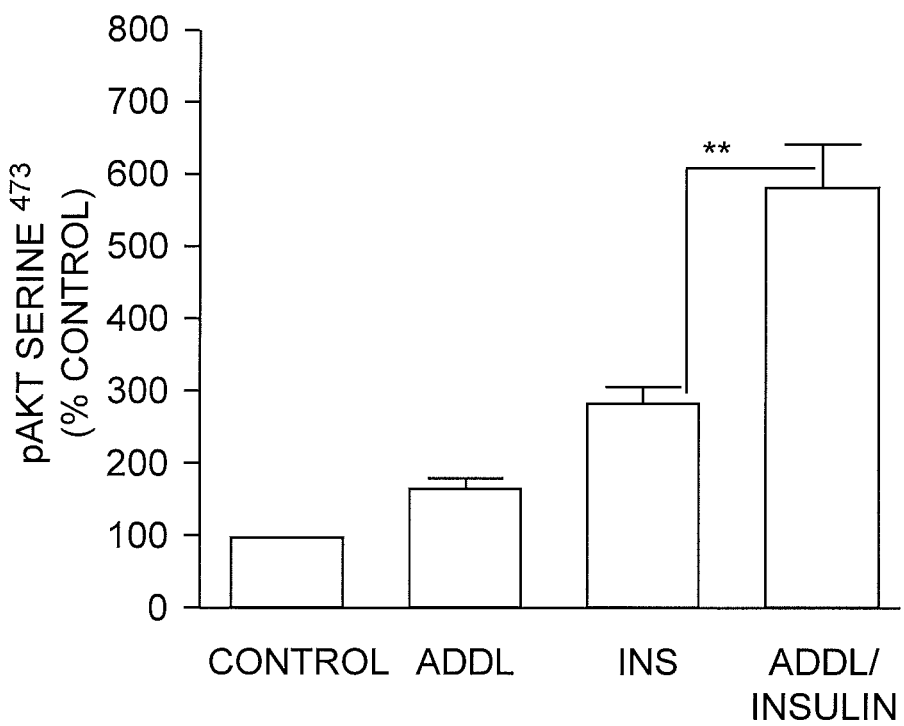
Figure 9B:
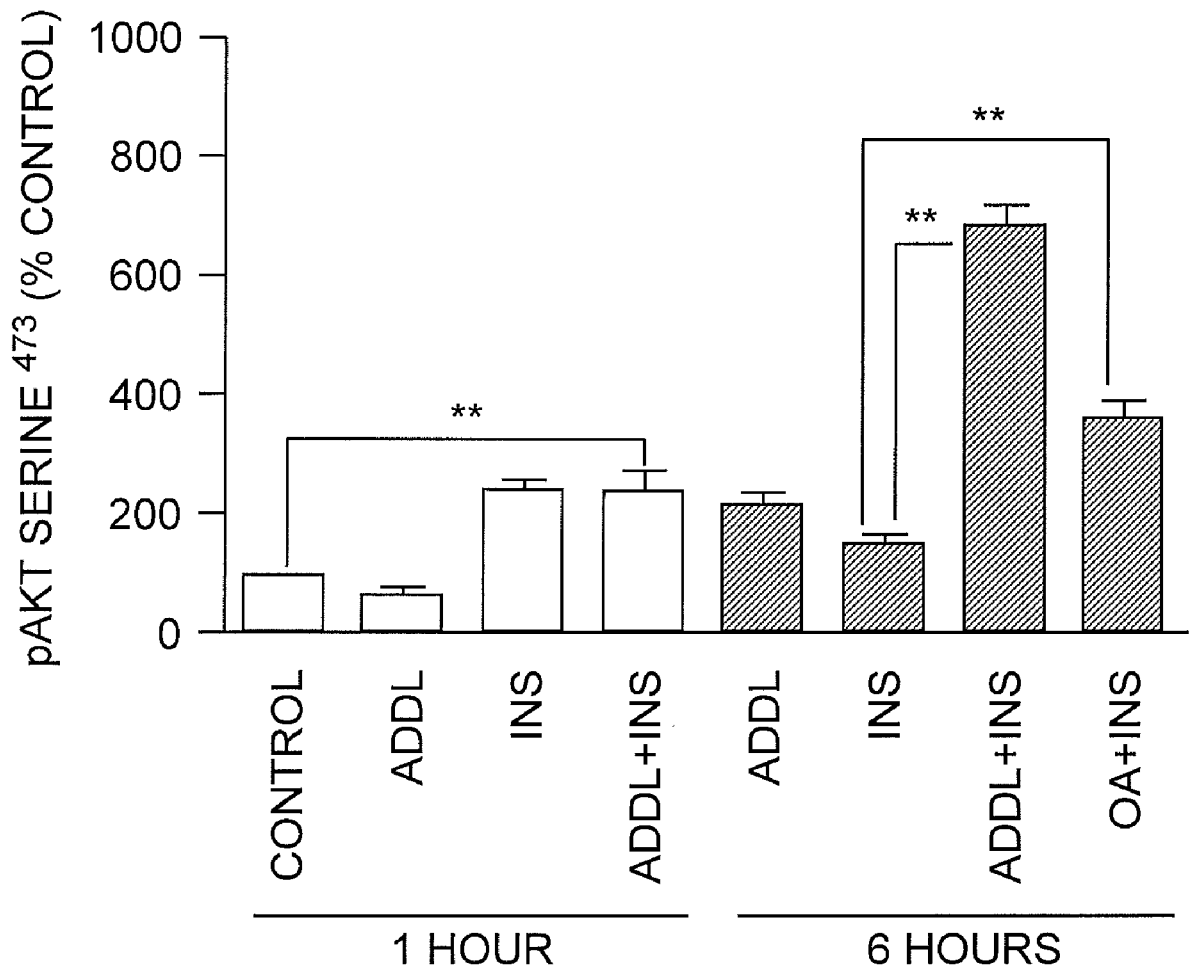

ADDLs Induce Insulin Resistance at Levels of Akt. Further downstream, insulin resistance can be associated with increased serine phosphorylation of Akt. Under normal conditions, insulin stimulation induces activation of Akt which undergoes phosphorylation at threonine 308 (pThr308) and serine 473 (pSer473). While pThr308 is involved in normal cellular functions such as glucose transport and cell survival, pSer473 plays a role in counter regulation of insulin receptor activity. Here it is shown that ADDLs caused an enhancement of the insulin-induced pAkt Ser473 in hippocampal neurons at 1 hour post-ADDL/INS treatment (FIG. 9A). The ADDL-enhanced pAkt ser473 was observed in cortical neurons at a later post-treatment stage (FIG. 9B). After an initial increase at 1 hour post-treatment, the insulin-induced pAkt ser473 was significantly dephosphorylated toward the control level at 6 hour post-treatment, indicating a normal recovery. In the presence ADDLs, however, there was an increase in pAkt ser473. Moreover, the insulin-induced increases in pakt ser473 were significantly prolonged by ADDLs. The prolonged pAkt ser473 indicates that the dephosphorylation mechanism such as serine/threonine phosphatases may be interrupted by ADDLs. To test whether inhibition of phosphatase 2A (PP2A) causes a similar enhancement of pAkt ser473, the cortical neurons were pre-treated with okadaic acid (OA), a potent PP2A/PP1 inhibitor at a concentration (10 nM) preferentially inhibiting PP2A. The cells were than incubated with insulin for 6 hours. It was shown that OA also prolonged the insulin-increased pAkt ser473 similar to that caused by ADDLs. These results indicate that it is possible that a long-term action of ADDLs inhibited neuronal PP2A leading to interruption of dephosphorylation of pAkt ser473. Enhanced pAkt ser473 in turn inhibits insulin receptor activity. The fact that ADDLs caused enhancement of pAkt ser473 at a much earlier time in hippocampal neurons indicates that the dephosphorylation system including PP2A in those neurons can be more vulnerable to ADDL insults.

Consequence of CNS Insulin Resistance—Insulin Receptor Plays an Important Role in ADDL Clearance, and Impairment of Insulin Receptor Activity Results in ADDL Accumulation. Results herein show that normal insulin receptor activity plays a role in the break down of ADDLs, and also is essential for preventing ADDL accumulation. Cells that do not express insulin receptor were not able to digest ADDLs added exogenously. There were no differences in the amount of ADDLs in the extracellular medium in the presence or absence of insulin. When those cells over expressed human insulin receptor, however, the exogenously applied ADDLs were reduced to Aβ monomers. In the presence of insulin, the amount of ADDL and Aβ monomers were markedly reduced. In contrast, inhibition of insulin receptor by AG1024 caused a striking accumulation of ADDLs in the extracellular medium. Similar results were observed in cultured cortical neurons. These results indicate that the abundance of insulin receptor in the cell is correlated with cell's ability to digest ADDLS. The fact that inhibition of insulin receptor caused massive aggregation of ADDLs indicates that healthy insulin receptor activity is essential for prevention of ADDL formation. Therefore, a regulatory molecular loop is contemplated in which 1) insulin receptor in the brain provides an essential mechanism for maintenance of the normality of Aβ metabolism; and 2) insulin receptor signaling itself is susceptible to insults of ADDLs. Chronic accumulation of ADDLs in the brain can interfere with activity of insulin receptor and downstream molecules, which can further worsen ADDL accumulation. Moreover, impairment of insulin receptor signaling can also compromise its functions in synaptic plasticity and learning/memory processing, as well as neuronal survival.

EXAMPLE 3

ADDL Binding and Insulin Receptor Levels

For ADDLs to impair insulin receptors, ADDL binding sites and insulin receptors should occur on the same neurons. This was investigated using cultures of mature hippocampal neurons, which have been shown to develop clusters of ADDL binding sites specifically at synapses (Lacor, et al. (2004)). ADDLs were added to cultures at 100 nM and incubated for 30 minutes to allow for complete binding. ADDL binding sites exhibited the same punctate distribution previously seen. Insulin receptors, identified using antibodies against the outward-directed alpha sub-unit, also distributed in a punctate manner. ADDL binding occurred on neurons that expressed insulin receptors, although not on all of them (~40% of neurons had insulin receptors but no ADDL binding). Most significantly, however, the subcellular distribution of insulin receptors was strikingly different on neurons with and without bound ADDLs. Neurons with ADDL binding showed virtual absence of insulin receptor immunoreactivity on their dendrites. Reciprocally, dendrites with abundant insulin receptors showed no ADDL binding. By image analysis, dendrites with ADDL binding had ~70% less insulin receptor immunoreactivity than the ADDL-free cells.

Differential distribution of ADDL binding sites and insulin receptors strongly indicates that ADDLs cause dendritic insulin receptors to down-regulate. However, an alternative possibility is that ADDLs attached only to dendrites that did not express insulin receptors. This alternative was not the case, as control cultures (not exposed to ADDLs) were observed to express insulin receptors in 100% of their dendrites (40 neurons selected by phase and then assessed for insulin receptor signal. This indicates that ADDLs did not target dendrites lacking insulin receptors but rather caused dendritic insulin receptor down-regulation.

Significantly, ADDL-bound neurons that lacked dendritic insulin receptors exhibited high levels of receptors within their cell bodies. In fact, in ADDL-positive neurons, insulin receptor immunoreactivity in cell bodies was elevated ~3-fold compared to levels in ADDL-free cells. The possibility thus existed that ADDLs triggered a major redistribution of insulin receptors without causing reduction in total receptor level, a possibility supported by western blot data. Because of the ADDL-induced loss of dendritic insulin receptors, it was subsequently determined whether ADDLs also caused loss of insulin receptor function. These experiments focused on the impact of ADDLs on insulin-induced receptor protein tyrosine kinase activity.

To investigate whether ADDLs cause IR impairment, changes in neuronal IR levels following ADDL treatment were analyzed. ADDLs prepared from synthetic Aβ showed a profile on western blots with the major species being trimer, tetramer and 12mer, consistent with previous reports (Gong, et al. (2003) supra; Lacor, et al. (2004) supra). To detect neuronal surface IR, an antibody recognizing the alpha subunit of IR (IRα) localized on the extracellular membrane layer. Abundant IRα immunoreactivity was detected in cultured hippocampal neurons, which was particularly concentrated on the membrane of soma and dendrites. After treated with 100 nM ADDLs for 30 minutes, however, there was a drastic change in IRα immunostaining pattern with a substantial reduction of IRα from dendrites but an increase in the cell body. Quantification of dendritic IRα fluorescent intensity revealed a significant loss of IRα immunoreactivity ($P<0.01$) following ADDL treatment (FIG. 10). These results clearly show that ADDLs induced removal of dendritic IR. The increased cytosolic IRα immunoreactivity implicates internalization of the receptor. Loss of IRα occurred specifically to ADDL attacked dendrites. Therefore, using a double-labeling protocol, colocalization of ADDL binding sites and insulin receptors was examined. Similar to the above experiment, ADDLs were added to cultures at 100 nM and incubated for 30 minutes to allow for complete binding. The results showed a striking differential distribution of ADDL binding and IRα immunoreactivity. Dendrites with robust ADDL binding showed virtual absence of insulin receptor immunoreactivity. Reciprocally, dendrites with insulin receptors showed little or no ADDL binding. By image analysis, the dendrites with ADDL binding had ~70% less insulin receptor immunoreactivity than the ADDL-free cells. These results thus indicate that loss of dendritic IR is clearly correlated with ADDL binding.

Interestingly, even though neurons that bound ADDLs showed an absence of insulin receptors on their dendrites, these same neurons exhibited high levels of insulin receptor immunoreactivity within their cell bodies. In fact, the insulin receptor immunoreactivity in these cell bodies was elevated ~3-fold compared to that measured in ADDL-free cells (FIG. 11); whereas on those neurons that lacked ADDL binding, IRα immunoreactivity was clearly concentrated on the membrane and dendritic processes. Similar IR distribution was observed in neurons without ADDL treatment. This observation indicates that insulin receptors were removed from the dendritic plasma membrane and not replaced during the 30-minute incubation with ADDLs. The down-regulation of IR is likely due to internalization the receptor by ADDLs.

Although the data indicate down-regulation of dendritic insulin receptors, it is possible that ADDLs might attach only to dendrites that do not express insulin receptors. This possibility seems unlikely, however, given the abundance of insulin receptors in cell bodies of ADDL-exposed neurons. Other experiments also make it clear that ADDLs bind to insulin receptor-containing neurons. For example, when cells were first incubated with insulin (1 micromolar; 30 minutes) before addition of ADDLs, then ADDL binding and its effects were blocked. In this regard, previous studies have reported that insulin at this dose maximally affects hippocampal plasticity (Huang, et al. (2003) *Mol. Cell. Neurosci.* 24(3):831-41). Most importantly with respect to the question of dendritic distribution, control cultures (not exposed to ADDLs) were observed to express insulin receptors in 100% of their dendrites (20 neurons selected by phase and then assessed for insulin receptor signal). It thus is clear that ADDLs do not target dendrites lacking insulin receptors but rather cause insulin receptors on dendrites to down-regulate.

Because these observations indicated that ADDLs cause loss of insulin receptors from dendrites, it was determined ADDL binding to insulin receptors could be block. Accordingly, mature hippocampal neurons were pretreated with 100 nM insulin or 1 μM insulin and subsequently treated with 100 nM ADDLs. The results of this analysis indicated that pre-incubation of cells with 100 nM insulin could prevent ~40% of ADDL binding to hippocampal neurons, whereas pre-incubation with 1 μM insulin prevented ~70% of ADDL binding to hippocampal neurons.

What is claimed is:

1. A method for enhancing the cellular uptake of soluble amyloid beta oligomers comprising contacting a cultured cell which expresses an insulin receptor with insulin or an insulin analog that enhances insulin receptor signaling and determining whether the insulin or insulin analog enhances cellular uptake of soluble amyloid beta oligomers thereby enhancing cellular uptake of soluble amyloid beta oligomers.

2. A method for treating a disease associated with soluble amyloid beta oligomers comprising administering to a subject in need of treatment an effective amount of Glulisine insulin or Detemir insulin that enhances cellular uptake of soluble amyloid beta oligomers in the brain of the subject and determining whether the insulin or insulin analog enhances cellular uptake of soluble amyloid beta oligomers thereby treating the disease associated with soluble amyloid beta oligomers.

* * * * *